(12) United States Patent
Tonelli et al.

(10) Patent No.: US 8,771,215 B2
(45) Date of Patent: Jul. 8, 2014

(54) MACHINE FOR EXTRACORPOREAL TREATMENT OF BLOOD

(75) Inventors: Claudio Tonelli, Modena (IT); Bernd Wittner, Cambridge (GB); Werner Beck, Rottenburg (DE); Helmut Hildwein, Tuebingen (DE); Reinhold Deppisch, Hechingen (DE); Jonas Svensson, Angelholm (SE); Bjorn Ericson, Lund (SE)

(73) Assignee: Cambro Lundia AB, Lund (SE)

( * ) Notice: Subject to any disclaimer, the term of this patent is extended or adjusted under 35 U.S.C. 154(b) by 454 days.

(21) Appl. No.: 13/331,728

(22) Filed: Dec. 20, 2011

(65) Prior Publication Data

US 2012/0095381 A1  Apr. 19, 2012

Related U.S. Application Data

(63) Continuation of application No. 11/632,751, filed as application No. PCT/IB2005/001482 on May 27, 2005, now Pat. No. 8,105,260.

(30) Foreign Application Priority Data

Jul. 23, 2004 (IT) ............... MO2004A0191

(51) Int. Cl.
*A61M 37/00* (2006.01)
*C02F 1/44* (2006.01)
*A61M 1/34* (2006.01)
*A61M 1/16* (2006.01)
*A61M 1/36* (2006.01)

(52) U.S. Cl.
CPC ............... *A61M 1/16* (2013.01); *A61M 1/3437* (2014.02); *A61M 2205/60* (2013.01); *A61M 2205/52* (2013.01); *A61M 1/3441* (2013.01); *A61M 1/1615* (2014.02); *A61M 1/3431* (2014.02); *A61M 1/1613* (2014.02); *A61M 1/3434* (2014.02); *A61M 1/3639* (2013.01); *A61M 1/1647* (2014.02); *A61M 1/3465* (2014.02)
USPC ....... 604/6.09; 604/5.04; 604/6.06; 604/6.11; 210/646

(58) Field of Classification Search
CPC ...... A61M 1/34; A61M 1/342; A61M 1/3441
USPC ........... 604/4.01, 5.01, 5.04, 6.09, 6.11, 6.06; 210/645, 646, 739, 741
See application file for complete search history.

(56) References Cited

U.S. PATENT DOCUMENTS

| 4,606,826 | A | 8/1986 | Sano et al. |
| 5,507,723 | A | 4/1996 | Keshaviah |
| 2002/0147423 | A1 | 10/2002 | Burbank et al. |

FOREIGN PATENT DOCUMENTS

| EP | 0 711 182 B1 | 5/1996 |
| JP | 61-119276 A | 6/1986 |
| JP | 1-201263 A | 8/1989 |

(Continued)

*Primary Examiner* — Leslie Deak
(74) *Attorney, Agent, or Firm* — Pearne & Gordon LLP (57) ABSTRACT

A machine (1) for extracorporeal blood treatment comprises a device (2) for ultrafiltration of a liquid through a semipermeable membrane (3) of a blood treatment device (4), a first sensor (11) for ultrafiltration rate through the membrane, a second group of sensors (13) for measuring a trans-membrane pressure, an infusion line (16) with an infusion pump (17) and a programmed controller (14) for calculating a maximum infusion rate as a function of the transmembrane pressure. The machine is suitable for kidney failure treatments, such as hemofiltration and hemodiafiltration. In a relatively short time the machine enables a large quantity of corporeal blood to be removed from the patient.

21 Claims, 5 Drawing Sheets

(56) References Cited

FOREIGN PATENT DOCUMENTS

| | | |
|---|---|---|
| JP | 6-501188 A | 2/1994 |
| JP | 60-49137 B2 | 6/1994 |
| JP | 2003-505209 A | 2/2003 |
| JP | 2003-116985 A | 4/2003 |
| WO | 86/02858 A1 | 5/1986 |
| WO | 93/01845 A1 | 2/1993 |
| WO | 01/08723 A1 | 2/2001 |

MACHINE FOR EXTRACORPOREAL TREATMENT OF BLOOD

BACKGROUND OF THE INVENTION

The invention relates to a machine and a procedure for extracorporeal treatment of blood.

Specifically, though not exclusively, the invention can be usefully applied in treatments involving an ultrafiltration of liquid through a semipermeable membrane, for example treatments for kidney failure such as pure ultrafiltration, hemofiltration, hemodialysis, and hemodiafiltration.

Extra-corporeal blood treatments generally involve removing blood from a patient, transporting it externally of the human body and reintroducing it to the patient once treated.

Treatments for kidney failure comprise, in general, both addition and/or removal of solutes from the blood, and removal of liquid.

As is well known, dialysis treatment is usually done by first removing blood from the patient and conducting it internally of a dialysis filter in which an exchange of solutes and liquid is performed through a semi-permeable membrane.

Various different typologies for dialysis treatment are known.

In pure ultrafiltration, the liquid to be removed is taken from the blood by pressure-gradient ultrafiltration through a semipermeable membrane, and is conveyed into a non-blood chamber of the filter. The solutes to be eliminated are drawn by convection along with the liquid, the convection transport being a contemporary transport of a liquid part of the blood and a part of the substances contained therein through the membrane.

In hemofiltration treatments, part of the liquid present in the blood crosses the membrane by ultrafiltration, drawing along with it, by convection, a part of the substances present in the blood, as in ultrafiltration treatment; also, a substituting fluid is infused into the blood before and/or after the filter, and in any case before the blood is returned to the patient.

In hemodialysis treatments, a sterile fluid of a predetermined composition is introduced into the non-blood chamber of the filter. The removal of liquid from the blood through the semipermeable membrane occurs by pressure-gradient ultrafiltration. The solute exchange through the membrane is essentially achieved by diffusion due to the concentration gradient of the solutes. A small part of the solutes is removed by convection along with the ultrafiltered liquid. In hemodialysis treatments no substitution fluid is used.

In hemodiafiltration treatments, the blood and the sterile fluid exchange substances both by diffusion and by convection, as in hemodialysis; in addition, a substitution liquid is infused into the blood as in hemofiltration treatments. The liquid is removed by ultrafiltration.

All the above types of dialysis treatment enable removal of an excess of liquid from the patient's body. The total quantity of liquid removed from the start to the end of the treatment (total weight loss) is one of the most important parameters in the treatment, and is generally set at the start of treatment as a target.

A further important parameter is the total treatment time.

In some treatments it is usual to pre-set the quantity of liquid removed from the patient per unit of time (also known as the weight loss rate). Usually the weight loss rate is set to a constant value or to a predefined profile. In any case, if a total weight loss value is added to the weight loss rate, the treatment time is determined a priori.

We observe in passing that the weight loss rate is equal, in general, to the difference between the ultrafiltration rate through the filter membrane and the flow rate of the substitution liquid (infusion rate). Also, in the case of hemodialysis or hemodiafiltration, the ultrafiltration rate is the same as the difference between the used dialysis fluid rate at the outlet of the non-blood filter chamber and the fresh dialysis fluid rate at the inlet of the non-blood chamber, while in the case of pure ultrafiltration or hemofiltration, the ultrafiltration rate coincides with the used fluid rate at the outlet of the non-blood chamber of the filter.

In the above-cited case, in which the weight loss rate is determined at start of treatment, if the infusion rate is also pre-set, then consequently the ultrafiltration rate will also be predetermined, as the sum of the weight loss rate and the infusion rate. The ultrafiltration actuators will therefore be controlled so that the ultrafiltration rate will follow the pre-set progression.

This type of control is essentially based on one or more of the flow rates of the liquids circulating in the dialysis machine (fresh dialysis liquid, used dialysis liquid, substitution liquid).

Apart from controls based on the flow rates, another known control is based on the trans-membrane pressure on the semipermeable membrane of the dialysis filter. In this case the total weight loss is usually pre-set (or another desired target, such as for example the total quantity of a certain metabolite to be removed from the patient), and the trans-membrane pressure is also pre-set, usually to a constant value for the whole treatment. The ultrafiltration actuators are controlled so that the pressure follows the pre-set progression. The treatment terminates when the overall weight loss (or the other target parameter) is reached. In an HF/HDF treatment and in trans-membrane pressure controlled mode, if the total patient weight loss and the total substitution volume infused to the patient are predetermined, then the treatment time is not predeterminable. It is possible to set a predetermined treatment time even in pressure controlled mode; however if the total patient ultrafiltration volume (or the total patient weight loss) is predetermined as well, the total substitution volume will not be predeterminable.

A further important parameter which is usually pre-set at the start of treatment is the flow rate of the blood removed from the patient, which crosses the extracorporeal circuit. The choice of this parameter depends on various factors, not least the state of the patient's vascular access. The blood flow rate considerably influences both the quantity of solutes exchangeable per time unit, and the quantity of liquid removable per time unit, so the treatment time largely depends on the blood flow rate, i.e. the time in which the prefixed target (weight loss or quantity of metabolite removed or volume of substituting liquid infused or others) is reached.

Normally the blood rate is a pre-set value determined by the operator. EP 0 711 182 describes however a case in which the blood flow rate is determined by the dialysis machine, at start of or during treatment. In the system of EP 0 711 182 the blood flow rate, which is removed from the patient and sent to a dialysis filter, is varied in a predetermined sequence, after which the system measures the concentration of a metabolite (for example urea or creatinine, or uric acid) in the used dialysis liquid downstream of the filter, in order to determine a profile of the metabolite concentration in relation to the blood flow rate. The system thus determines the value of the blood flow rate which corresponds to the maximum metabolite concentration, and automatically sets the blood flow rate at the determined value. The system has the aim of optimizing blood purification performance with relation to the metabolite during the dialysis treatment. However, the system of EP 0 711 182 is not able to optimize the weight loss rate or the ultrafiltration rate. In other words, it does not guarantee to minimize the treatment time in cases where the pre-set target is a determined weight loss in the patient or a determined volume of substituting liquid to infuse in the patient.

WO 01/08723 discloses a method of optimizing the operating point of a dialysis filter. In WO 01/08723 a dialysis machine is controlled by calculating a filtration factor $FF=UFR/[Qb*(1-Hct)]$, in which UFR is the ultrafiltration rate, Qb is the blood flow rate, and Hct is the hematocrit (i.e. the concentration of red blood cells in the arterial blood), and by verification of whether the filtration factor FF is within an admissible range. If not, the ultrafiltration rate is altered so as to return the system to a non-critical operating point. If the filtration factor FF is acceptable, it is checked whether the ultrafiltration factor can be incremented to increase efficiency in conditions of safety. In particular WO 01/08723 teaches that, in the case of increased deviation between the calculated filtration factor FF and the maximum limit set (for example in the case of previous reduction of ultrafiltration), the operating conditions can be modified so as to increase the efficiency of filtration, in particular by increasing the ultrafiltration rate. This makes it possible to modify the operating conditions of the filter dynamically during the treatment, following any variations and fluctuations of the hematocrit in the course of treatment, to obtain conditions of safety and increased efficiency at every instant. However, the method for increasing filter efficiency disclosed by WO 01/08723 is susceptible of improvement.

SUMMARY OF THE INVENTION

A main aim of the present invention is to provide a machine for extracorporeal blood treatment which is able to remove, in a relatively short time, a large quantity of corporeal liquid from a patient.

A further aim of the invention is to realise a control procedure for an ultrafiltration system which can optimize the efficiency of the weight loss of a patient undergoing dialysis.

An advantage of the invention is that it reduces the treatment time for a same quantity of corporeal fluid to be removed from a patient, or increases the quantity of fluid removed for a same treatment time.

A further advantage of the present invention is that it exploits to the fullest the ability of the semi-permeable membrane performing the extracorporeal blood treatment.

A further advantage is that it is suited to the conditions of the patient at the start of treatment.

A further advantage is that it is adaptable to the conditions of the patient-machine system which are variable during a treatment.

By monitoring the ultrafiltration system during the treatment time, the invention enables automatic regulation of the working conditions of the ultrafiltration system in order to follow, during treatment, both variations in the filter performance and variations in the characteristics of the patient's blood.

Furthermore, the invention causes the ultrafiltration system to work at optimum performance levels, whatever the blood treatment device used during the course of the treatment, and whatever the condition of the patient at start of treatment. In this context it should be noted that patient's blood composition, which influences the type, shape and maximum of the curve of ultrafiltration rate as a function of TMP, depends on many factors, e.g. EPO, dose, use of aspirin, antibiotics, anti-inflammatory drugs etc., and these factors may change without any prior notice or indication. The invention has an advantage to provide a controller that in this case also can detect changes of parameters depending on patient's blood composition and so can provide an historical analysis that could be useful for better treatment delivery and less operations complications, e.g. decreased efficiency, exchange of the system after clotting, etc.

The invention provides a control system that enables a better automation of a blood treatment by prospective setting of treatment parameters. The invention enables a better system compatibility between the variations of patient's blood composition, the type of the dialyser (with a certain bandwidth, variation of the ultrafiltration coefficient, fiber diameters, etc.) and the dialysis machine controlling and operating functions.

The invention has a further advantage to prevent filter clotting due to higher hematocrit.

These aims and advantages and more besides are all attained by the invention as it is characterised in one or more the accompanying claims.

In a specific embodiment of the invention, an optimal operating condition of an ultrafiltration device is determined by means of detecting, in two different operating conditions of the ultrafiltration system, at least two values of the ultrafiltration rate, and by a subsequent comparison of the values in order to determine a maximum ultrafiltration rate value.

In a specific embodiment of the invention, an optimal operating condition of an ultrafiltration device is determined by means of detecting, in two different operating conditions of the ultrafiltration system, at least two values of the ultrafiltration rate, at least two values of a quantity indicative of an operating situation of the ultrafiltration system (for example a trans-membrane pressure or a velocity of an ultrafiltration pump), and by means of a subsequent control determining whether the values satisfy or not a predetermined relation with a reference value.

In a specific embodiment of the invention, an optimal operating condition of an ultrafiltration system is sought by means of determining a derivative of the ultrafiltration rate, as a function of a quantity which is indicative of an operating situation of the ultrafiltration system (for example a transmembrane pressure or a velocity of an ultrafiltration pump), and a control on whether the derivative satisfies or not a predetermined relation with a limit reference value. This control can comprise an evaluation of whether the derivative is positive and less than a chosen small predefined value.

In a specific embodiment of the invention, the search for an optimal operating condition of an ultrafiltration system is carried out periodically, in particular at predetermined time intervals. This enables an adaptation of the ultrafiltration system to a change in the effective optimal operating condition, which change is essentially (but not only) due to the fact that the semipermeable membrane, during the course of the treatment, varies in performance levels. It has been observed, for example, that during treatment the profile of ultrafiltration rate as a function of the transmembrane pressure usually changes: thanks to a periodic updating of the sought-after optimal operating condition, the variation in the characteristics of the semipermeable membrane can be accounted for. Furthermore, by periodically performing a search for an optimal operating condition of the ultrafiltration system (transmembrane pressure scan), the operating conditions of the filter will change with the consequent, at least partial unclotting of the filter, resulting in better filter/treatment performance throughout the remaining treatment. The search for an optimal operating condition of the ultrafiltration system can be performed continuously by running the control algorithm throughout the treatment.

In a specific embodiment of the invention, the search for an optimal operating condition for an ultrafiltration system involves increasing and/or reducing the ultrafiltration flow rate (for example by increasing and/or reducing the operating velocity of an ultrafiltration actuator by a predetermined quantity), measuring the transmembrane pressure and checking whether the transmembrane pressure undergoes an excessive change consequent to a determined change in the ultrafiltration rate.

In a specific embodiment of the invention, a profile of the ultrafiltration flow rate as a function of the transmembrane pressure is made, and an optimal operating situation is set up, corresponding to or based on the maximum of the profile obtained previously.

In a specific embodiment of the invention, a plurality of optimal operating conditions are calculated, each of which corresponds to a set value of the flow rate of the liquid at the inlet of the blood treatment device, after which there is a further calculation from among the determined plurality of optimal conditions of the one which gives the greatest ultrafiltration rate.

Further characteristics and advantages of the present invention will better emerge from the detailed description that follows of at least one embodiment of the invention, illustrated by way of non-limiting example in the accompanying figures of the drawings.

BRIEF DESCRIPTION OF THE DRAWINGS

The following description will be made with reference to the accompanying figures of the drawings, which are included for the purposes of illustration and are therefore non-limiting, and in which.

DETAILED DESCRIPTION

Figure 1:
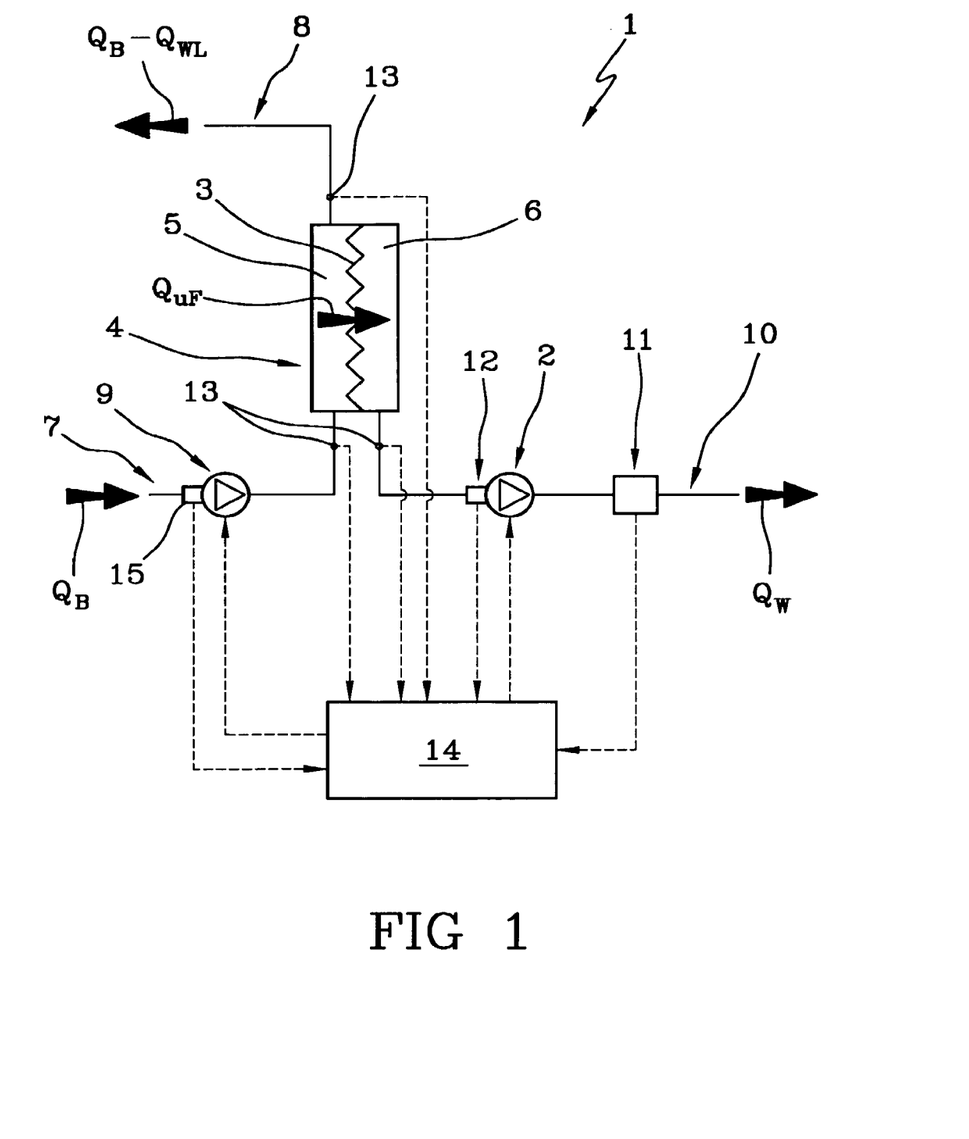
FIG. 1 is a diagram of a machine for pure ultrafiltration treatment.

With reference to FIG. 1, 1 denotes in its entirety a machine for extracorporeal blood treatment. In particular, the machine of FIG. 1 is suitable for performing a pure ultrafiltration treatment.

The machine 1 comprises an actuator 2 for ultrafiltration of a liquid through a semipermeable membrane 3 of a blood treatment device 4.

The blood treatment device comprises a blood chamber 5 and a fluid chamber 6, separated one from another by the semipermeable membrane 3.

An extracorporeal blood circuit comprises an arterial line 7, which takes the blood removed from a patient to an inlet of the blood chamber 5, and a venous line 8, which returns the treated blood from an outlet of the blood chamber 5 to the patient.

An actuator 9, comprising for example a peristaltic blood pump, causes the blood to circulate along the extracorporeal circuit, generating a blood flow rate $Q_B$ along the arterial line 7.

A discharge line 10 is connected to an outlet of the fluid chamber 6.

The ultrafiltration actuator 2 can be, as in the illustrated embodiment, a fluid circulation pump, such as for example a rotary pump or an alternating pump, arranged on the discharge line 5.

The ultrafiltration actuator 2 generates a flow rate $Q_W$ of a discharge fluid along the discharge line 10. The flow rate $Q_W$ of the discharge fluid corresponds, in the case of pure ultrafiltration, to the ultrafiltration flow rate $Q_{UF}$ through the semipermeable membrane 3.

The patient's weight loss rate $Q_{WL}$ in this case is $Q_{WL}=Q_{UF}=Q_W$.

The machine 1 comprises a sensor 11 for detecting the ultrafiltration flow rate $Q_{UF}$ through the membrane 3. In this case the sensor 11 comprises a flowmeter arranged on the discharge line 10 for measuring the discharge fluid flow rate $Q_W$. The flow rate sensor 11 can be any device of known type (gravimetric, magnetic, ultra-sound, Coriolis effect, turbine, etc.) suitable for measuring an ultrafiltration flow rate $Q_{UF}$ in an ultrafiltration system.

The machine comprises a sensor 12 of a quantity indicating an operating situation of the ultrafiltration system. In the illustrated embodiment, the quantity is the rotation velocity $\omega$ of the discharge fluid circulation pump along the discharge line 10. The sensor 12 can be, for example, a magnetic encoder for measuring the velocity $\omega$.

The machine 1 further comprises another sensor 13 for detecting another quantity indicating an operating situation of the ultrafiltration system. In the example this other quantity is a transmembrane pressure TMP. The sensor 13 comprises three pressure gauges arranged for measuring the pressure, respectively, at the inlet of the blood chamber 5, at the outlet of the blood chamber 5, and at the outlet of the fluid chamber 6.

The machine comprises a controller 14 predisposed to receive the signals supplied by the sensors 11, 12 and 13, and for supplying command signals to the actuators 2 and 9. The controller 14 is also able to calculate a transmembrane pressure on the basis of the pressure values received from the sensor 13.

The controller 14 is programmed to perform the following operations:

changing (increasing and/or lowering) at least one operating parameter of the ultrafiltration actuator 2; in this case the parameter is the velocity of rotation $\omega$;

determining a change in the ultrafiltration flow rate $\Delta Q_{UF}$ by effect of the above-mentioned change;

determining a change in the transmembrane pressure $\Delta TMP$ by effect of the above-mentioned change;

checking whether the above-mentioned changes $\Delta Q_{UF}$ and $\Delta TMP$ satisfy the following predetermined relation with a reference limit value $\epsilon$, where $\epsilon$ is a constant value close to zero: $\Delta Q_{UF}/\Delta TMP \leq \epsilon$;

generating a signal consequent to the above-mentioned check.

The controller 14, in substance, generates a procedure for finding a maximum or nearly-maximum value for the ultrafiltration flow rate $Q_{UF}$ as a function of the transmembrane pressure TMP.

The controller 14 is programmed to perform the above operations during the treatment, e.g. at the start of the treatment and/or in the course of the treatment.

If the controller 14 finds that $\Delta Q_{UF}/\Delta TMP > \epsilon$, it generates a signal by which the above-described operations are repeated, at a different value for the angular velocity $\omega$ of the ultrafiltration actuator 2.

If the controller 14 finds that $\Delta Q_{UF}/\Delta TMP \leq \epsilon$, it generates a signal by which the following operations are performed:

selection of a desired value $\Omega_{des}$ of the operating parameter of the ultrafiltration actuator 2; commanding the actuator 2 to operate at the selected value $\Omega_{des}$. If, for example, the phase of changing the operating parameter of the ultrafiltration actuator 2 comprises a passage from a first value $\Omega_1$ of the angular velocity of the actuator 2 to a second value $\Omega_2$, the above-mentioned desired value $\Omega_{des}$ can be selected according to $\Omega_1$ and/or $\Omega_2$; for example $\Omega_{des}=\Omega_1$, or $\Omega_{des}=\Omega_2$, or $\Omega_{des}=\Omega_2-\Delta\Omega$ (where $\Delta\Omega$ is a predetermined value being $\Delta\Omega<(\Omega_2-\Omega_1)$), or $\Omega_{des}=\Omega_1+\Delta\Omega$, or $\Omega_{des}=(\Omega_1+\Omega_2)/2$, or through other functions of $\Omega_1$ and/or $\Omega_2$.

The controller 14 is programmed to operate the ultrafiltration actuator 2 at the desired $\Omega_{des}$, (i.e. the value at which $Q_{UF}$ as a function of TMP has a maximum or, in any case, the derivative of $Q_{UF}$ as a function of TMP assumes a null or positive value which is inferior to a small value) for a predetermined time, for example 10-20 minutes, and, once this time has passed, is programmed to repeat the above-described operations in search of the maximum (or the zeroing of the derivative) of the function $Q_{UF}$(TMP). In substance, the controller 14 is programmed periodically to repeat the search operations for the maximum of the function $Q_{UF}$(TMP).

In a further embodiment, the controller 14, instead of verifying whether $\Delta Q_{UF}/\Delta TMP \leq \epsilon$, or additionally to doing so, verifies whether $\Delta Q_{UF}/\Delta\Omega \leq \eta$, where $\Delta\Omega$ is a variant (measured or set) of the angular velocity of the actuator 2, and $\eta$ is a predefined value close to zero.

In a further embodiment, the controller 14 is programmed to carry out the above-described operations to establish the maximum of function $Q_{UF}$(TMP), for at least two different values $Q_{B1}$ and $Q_{B2}$ of the flow rate $Q_B$ of the liquid to be subjected to ultrafiltration; the flow rate $Q_B$ can be correlated, in a known way, to a velocity $\psi$ of the blood pump detected, for example, by a sensor 15 associated to the pump itself. In substance the controller 14 determines a first value $\Omega_1$ of the velocity of the ultrafiltration pump, at which there is a first value $Q_{UF1}$ of the maximum of the function $Q_{UF}$(TMP), maintaining the blood pump at a constant velocity $\psi_1$; after which the velocity of the blood pump is changed, bringing it to a velocity of $\psi_2 \neq \psi_1$, and a second value $\Omega_2$ is determined to which a second maximum value $Q_{UF2}$ corresponds for the function $Q_{UF}$(TMP). The controller 14 is programmed to compare the results obtained in the two cases and to emit a signal consequent to the comparison; the controller 14 in effect checks which of the two values $Q_{UF1}$ and $Q_{UF2}$ is the greater and sets the machine to work at either the pair of values $(\psi_1, \Psi_1)$ or $(\psi_2, \Omega_2)$, corresponding to the value $Q_{UF1}$ or $Q_{UF2}$, according to which is the greater of the two values. The above-described procedure can be repeated for other values, $Q_{B3}, Q_{B4}, \ldots$, of the ultrafiltration liquid flow rate.

In a further embodiment, the controller 14 is programmed to perform a search for the maximum (or the value bringing the derivative to almost zero) of the function $Q_{UF}(\omega)$, that is, the ultrafiltration flow rate as a function of the velocity of the ultrafiltration actuator 2; or the controller 14 is programmed to perform a search for the maximum of the function $1/TMP(\omega)$, where $TMP(\omega)$ is the transmembrane pressure as a function of the velocity of the ultrafiltration actuator 2. The controller 14 is programmed to perform the following operations:

modifying at least one operating parameter of the ultrafiltration actuator 2, for example passing from velocity $\Omega_1$ to velocity $\Omega_2$;

determining a change in the ultrafiltration flow rate $\Delta Q_{UF}$, or the transmembrane pressure $\Delta TMP$, by effect of the above-described modification;

verifying whether the variation, $\Omega Q_{UF}$ or $\Delta TMP$, agrees with a predetermined relation with a reference limit value; this relation can consist in $\Delta Q_{UF} \leq (\Delta Q_{UF})_{min}$, where $(\Delta Q_{UF})_{min}$ is a minimum threshold value, or in $\Delta TMP \leq (\Delta TMP)_{max}$, where $(\Delta TMP)_{max}$ is a maximum threshold value;

generating a signal consequent to the above control, by which if $\Delta Q_{UF} \leq (\Delta Q_{UF})_{min}$, or if $\Delta TMP \geq (\Delta TMP)_{max}$, the value of $\omega$ is deemed to have been found, for which function $Q_{UF}(\omega)$, or function $1/TMP(\omega)$, expresses a maximum.

The change in velocity $\Delta\Omega=\Omega_2-\Omega_1$ can be a set or a measured value.

In substance, the above-described control procedures cause the ultrafiltration actuator to operate at a maximum ultrafiltration flow rate, considered as a function of another operating parameter of the ultrafiltration system, or in any case to operate at an ultrafiltration flow rate beyond which the derivative of the ultrafiltration flow rate, as a function of the other considered operating parameter, assumes a value which is very close to zero or is indeed negative, i.e. is at an ultrafiltration flow rate beyond which the operating condition of the semipermeable membrane would be considered critical.

The above-described procedures can be applied singly, or alternatingly, or contemporaneously in combination with one another.

The above-described procedures enable the ultrafiltration system to operate in optimal conditions in respect of the maximum weight loss $Q_{WL}$ of the patient.

Figure 2:
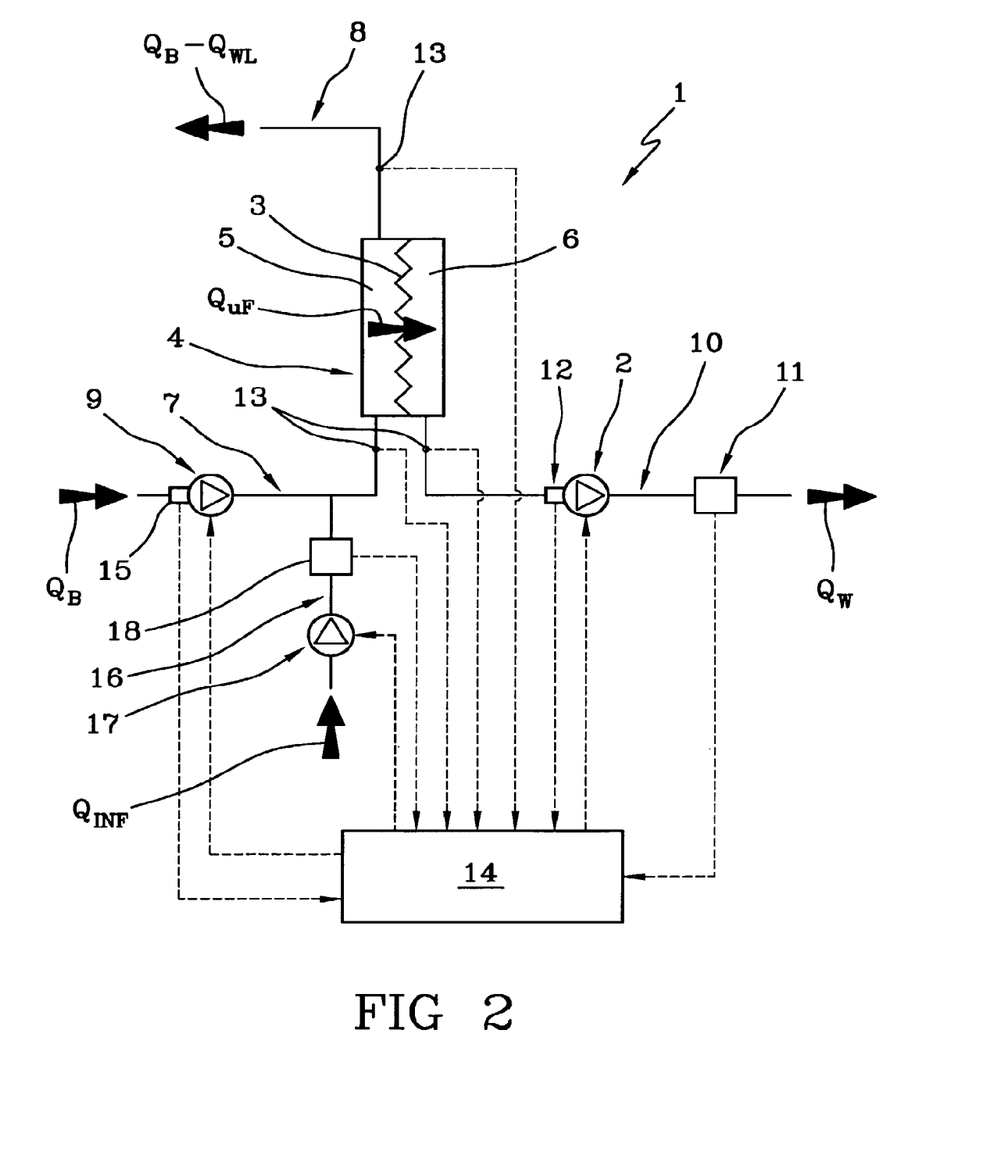
FIG. 2 is a diagram of a machine for hemofiltration treatment.

With reference to FIG. 2, 1 denotes in its entirety a machine for extracorporeal blood treatment. In particular, the machine of FIG. 2 is suitable for performing a hemofiltration treatment. For the sake of simplicity, the elements which are the same as in FIG. 1 have been denoted using the same numbers.

In particular, 2 denotes the ultrafiltration actuator, 3 the semipermeable membrane, 5 the blood chamber, 6 the fluid chamber, 7 the arterial line, 8 the venous line, 9 the blood circulation actuator, 10 the discharge line, $Q_W$ the discharge fluid flow rate along the discharge line.

In the case of hemofiltration an infusion line 16 is included for injecting into the extracorporeal blood a flow $Q_{INF}$ of substitution liquid, by means of an infusion actuator 17. In the illustrated embodiment, the substitution liquid is pre-infused upstream of the blood treatment device 4; in any case post-infusion is possible, downstream of the device 4, or a combined pre- and post-infusion.

In the case of hemofiltration the ultrafiltration flow rate is $Q_{UF}=Q_W$, while the patient weight loss rate is $Q_{WL}=Q_{UF}-Q_{INF}=Q_W-Q_{INF}$. The infusion rate is detected by means of a flow rate sensor 18.

Still in reference to FIG. 2, 11 denotes a sensor for detecting the ultrafiltration flow rate $Q_{UF}$, comprising a flowmeter for measuring the rate $Q_W$ of the discharge fluid, with 12 denoting the rotation velocity $\omega$ sensor of the discharge fluid circulation pump, 13 the transmembrane pressure sensor, 14 the controller receiving the signals emitted by the sensors 11, 12, 13, 15 and 18 and providing command signals to the actuators 2, 9 and 17, with 15 the sensor for the blood pump velocity.

The controller 14 is programmed to perform the search operations for the optimal condition of maximum rate of patient weight loss $Q_{WL}$ and follows the same modalities as described above in reference to pure ultrafiltration operations.

However, differently to FIG. 1, in this case the flow rate of the ultrafiltration liquid, or rather the liquid part of the ultrafiltration fluid, does not depend only on the patient's blood flow rate $Q_B$ and on the blood hematocrit level, but also on the infusion flow rate $Q_{INF}$. The above-described procedure which searches out the optimal conditions upon a variation not only of an operating parameter of the ultrafiltration actuator 2 but also of the ultrafiltration liquid flow rate, will have to take account of the fact that the flow rate is a function of both an operating parameter of the blood circulation actuator 9 and of an operating parameter of the pre-infusion liquid circulation actuator 17. The above-described procedure in this case may include varying either the blood circulation actuator 9 operating parameter or the pre-infusion actuator 17 operating parameter, or both parameters, then comparing the optimal conditions determined at each variation in order to choose, from among the various optimal conditions, the one which is considered the best overall, for example the condition in which the ultrafiltration flow rate $Q_{UF}$ is at the maximum.

The above-described procedures enable the ultrafiltration system to operate in optimal conditions in respect of the maximum ultrafiltration flow rate $Q_{UF}$ in order, for example, to achieve a maximum infusion rate of substitution liquid $Q_{INF}$ to the patient.

Figure 3:
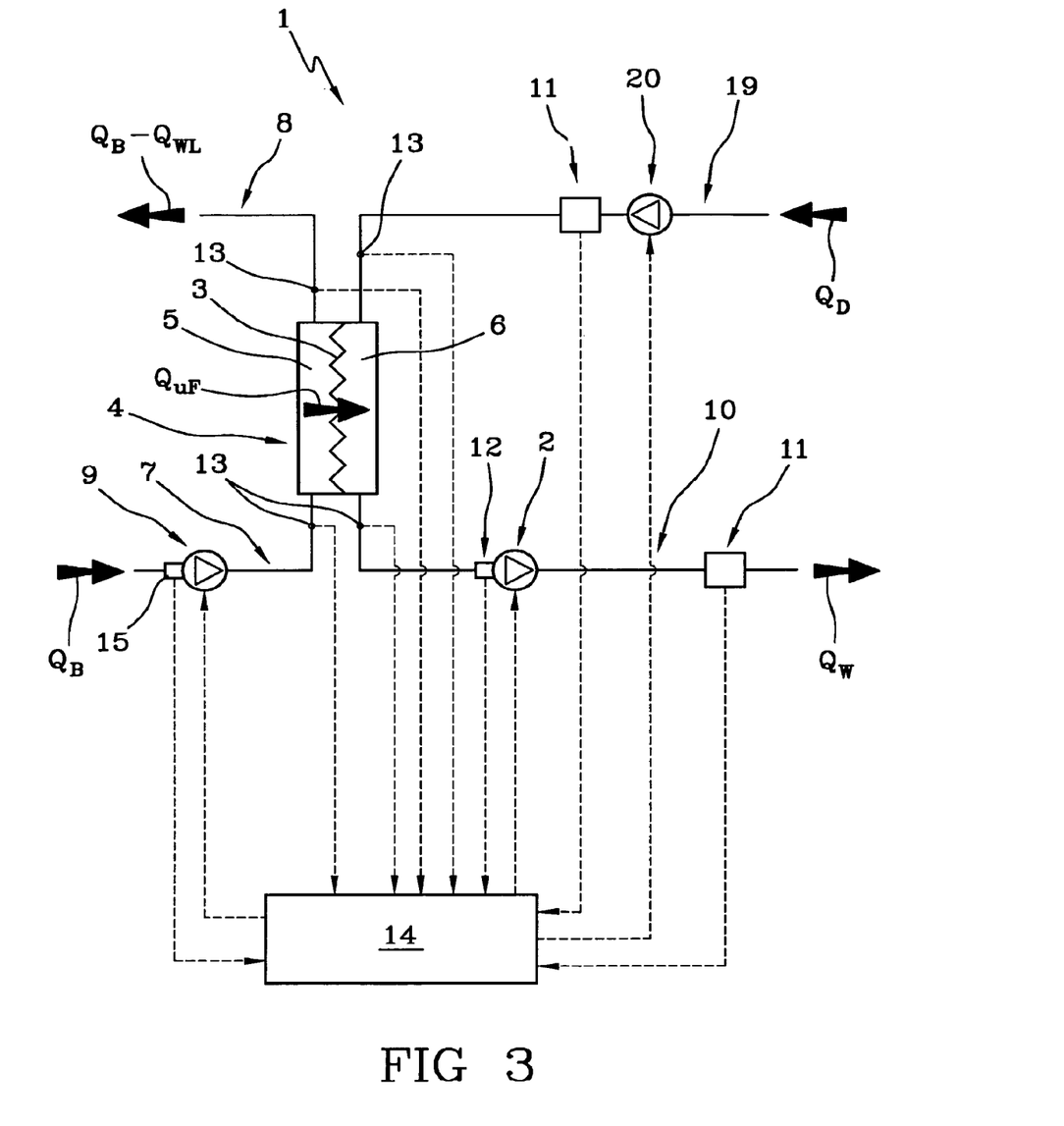
FIG. 3 is a diagram of a machine for a hemodialysis treatment.

With reference to FIG. 3, 1 denotes in its entirety a machine for extracorporeal blood treatment. In particular, the machine of FIG. 3 is suitable for performing a hemodialysis treatment. For the sake of simplicity, the elements which are identical to those in FIG. 1 are denoted by the same numbers.

The hemodialysis machine of FIG. 3 comprises a supply line for a fresh dialysis liquid 19, provided with a supply actuator 20, which circulates a flow $Q_D$ of liquid towards an inlet of the fluid chamber 6.

The transmembrane pressure TMP is calculated on the basis of pressure values detected at four points, i.e. at the three points already indicated herein above, and also at the inlet of the fluid chamber 6.

In the case of hemodialysis the ultrafiltration flow rate is $Q_{UF}=Q_W-Q_D$, while the patient weight loss rate is $Q_{WL}=Q_{UF}=Q_W-Q_D$.

The ultrafiltration flow rate sensor 11 comprises, in the illustrated embodiment, a $Q_W$ rate measuring device on the discharge line 10 and a $Q_D$ flow rate measuring device on the supply line 19. In other embodiments it is possible to use, as a sensor of the ultrafiltration flow rate, a differential measurement device which measures the difference of the rates $Q_W-Q_D$.

The procedures for searching for the optimal operating condition of the ultrafiltration system are essentially the same as the ones described herein above.

Figure 4:
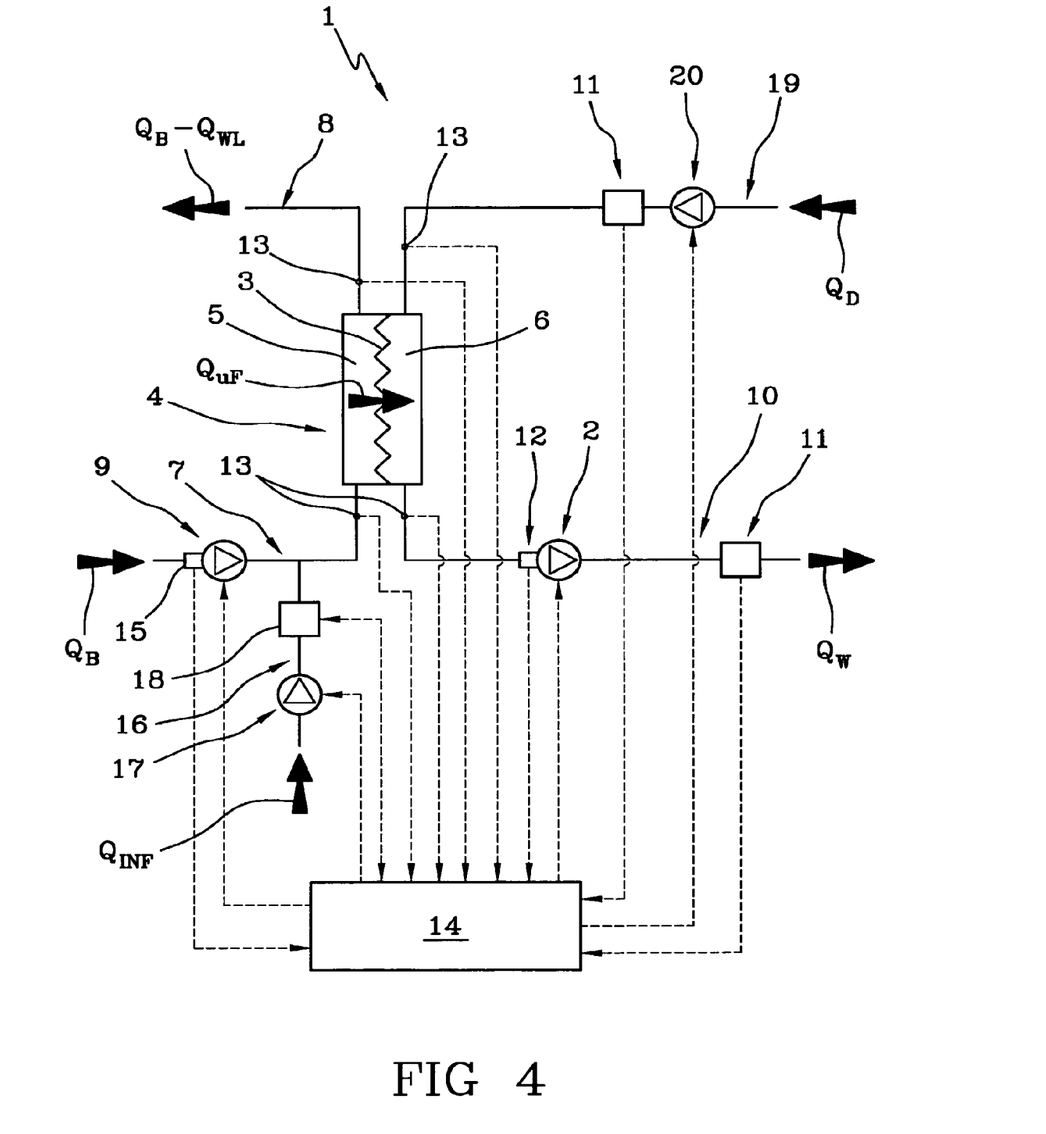
FIG. 4 is a diagram of a machine for hemodiafiltration treatment.

With reference to FIG. 4, 1 denotes in its entirety a machine for extracorporeal blood treatment. In particular, the machine of FIG. 4 is suitable for performing a hemodiafiltration treatment. For the sake of simplicity, the elements which are the same as in the machines of FIGS. 2 and 3 have been indicated using the same numbers.

In the case of hemodiafiltration, the ultrafiltration flow rate is $Q_{UF}=Q_W-Q_D$, while the patient weight loss rate is $Q_{WL}=Q_{UF}-Q_{INF}=Q_W-(Q_D+Q_{INF})$. An embodiment is possible in which the substitution liquid, flow rate $Q_{INF}$, comes from the supply line 19, where flow $Q_D$ runs. In this case the flow rate at the inlet of the fluid chamber 6 is $Q_D-Q_{INF}$, and therefore the ultrafiltration flow rate is $Q_{UF}=Q_W-(Q_D-Q_{INF})$, while the patient weight loss rate is $Q_{WL}=Q_{UF}-Q_{INF}=Q_W-Q_D$. An embodiment is possible in which the outlet line from the fluid chamber 6 is divided into an ultrafiltration line, where a liquid $Q_{UF}$ flows, and a discharge line, where a flow $Q_W$ runs, which is controlled so that $Q_W=Q_D$.

Other typologies can be used, of known type, for the ultrafiltration systems, such as for example a system in which the ultrafiltration is obtained by means of a pair of actuators, one operating on the arterial line and the other on the venous line.

In all the above-described ultrafiltration systems, and in other ultrafiltration systems of known type and not described, the procedures for seeking the maximum rate of ultrafiltration are similar to those described herein for the apparatus of FIGS. 1 and 2.

Figure 5:
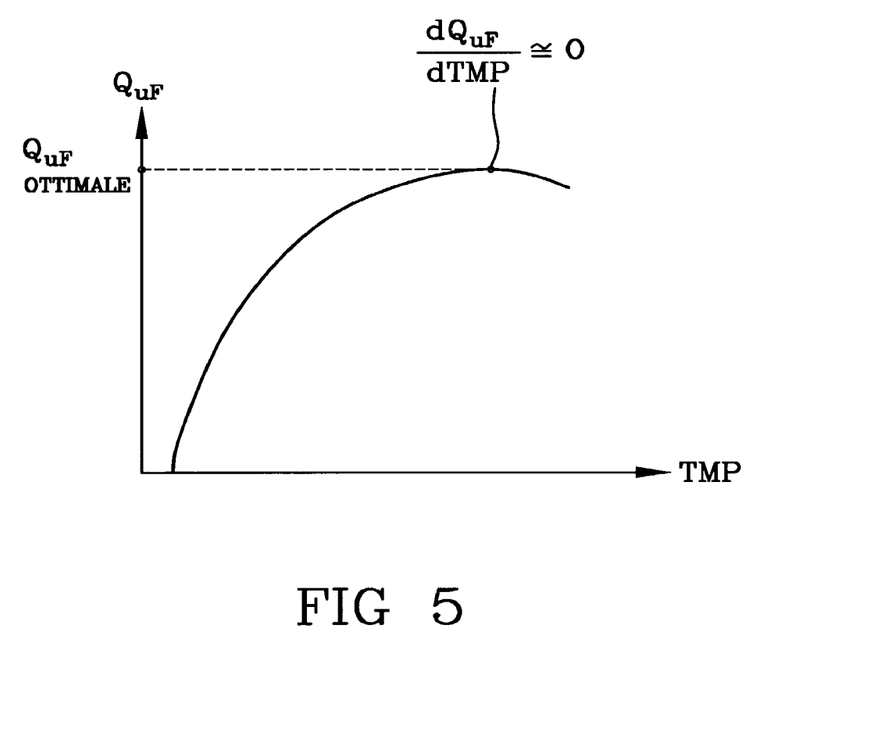
FIG. 5 is a profile of ultrafiltration rate as a function of transmembrane pressure.

The characteristics (shape, maximum, etc.) of the curve $Q_{UF}(TMP)$ reflect a patient specific pattern not only for a single treatment, but also along changes of the blood composition or disease stage, i.e. by changing/increasing blood viscosity and tendency to create clotting due to increase of fibrinogen as a result of acute inflammatory periods. Thanks to the proposed invention it is possible to compare curve profiles of a patient in an historical analysis (series of the last 3, 5, or 10 treatment records) so as to reduce complications in the treatment in a prospective/preventive manner.

EXAMPLE

HF/HDF Treatment

This example relates to an HDF or HF machine wherein the substitution liquid is withdrawn from a dialysis circuit for preparation on-line of a dialysis liquid. However, this example can be applied also to pressure controlled HF/HDF treatments of different types, as for example a HF/HDF treatment with a supply of dialysis liquid and/or substitution liquid from bags (e.g. LVHDF), or a HF/HDF with separate/independent supply of substitution liquid.

Before starting the treatment, the screen of the user interface of the machine is used to initiate an automatic TMP scan process or to switch between adjustable time and adjustable volume modes. The operator may press a key to start automatic scan to find optimum TMP (AUTO SETUP mode). In AUTO SETUP mode, the machine will automatically try to find the optimum TMP setting according to the following steps 1) to 5). The process can be fully automatic (no operator action required).

1) The operator sets the UF-volume and the pre- or post-dilution mode. Setting an initial TMP is optional but will decrease the time required to find the optimum TMP. This initial TMP will also be used as set TMP "fallback" if optimum TMP is not confirmed. The operator also sets an infusion volume or a treatment time.

2) By pressing a key, the machine will start the automatic TMP-scan process. The set TMP will be increased or decreased in steps to find the maximum UF-rate point. TMP-scan will start at the set TMP. If no initial TMP is set by the operator, the scan will start with a short period in volume control with a low infusion rate, for example depending on blood flow rate and/or on pre- or post-infusion mode (e.g. 50% of blood flow $Q_b$ if pre-dilution and 10% of $Q_b$ if post-dilution), in order to get a stable TMP start value.

3) If any limit (see below) is reached, the automatic scan will end and a confirmable attention will be issued.

4) If a true optimum (maximum total UF rate) is found, the machine will automatically lower the set TMP by a predetermined percentage, e.g. 10%, or by a predetermined value if optimum is in a predetermined range, e.g. by 10 mmHg if optimum is in the range −100 to +100 mmHg. In other embodiments the TMP is not adjusted or it is adjusted upwards.

5) When the scan has ended, the recommended TMP is used as a set value. The operator may confirm or not the new TMP.

The UF-process may be started or not during the optimization process. If started after optimum TMP has been selected, treatment time or infusion volume will change depending on mode.

After the scan is complete, the screen will allow the operator to choose from the following options 1) to 3).
1) Manually adjust the TMP.
2) Change from adjustable time mode to adjustable volume mode or vice versa. Changing to adjustable volume gives greater control over the delivered dialysis dose, while adjustable time fixes the end of treatment time for the patient. In practice, adjustable volume may be used in the beginning of the treatment, but near the end the operator may switch to adjustable time to accommodate for patient transportation and other logistical needs (next patient, etc.).
3) Change the substitution volume (if in adjustable volume mode) or change the treatment time (if in adjustable time mode).

Depending on mode, when one parameter (time or volume) is adjusted, the other (volume or time) will be recalculated in real time.

The following is a list of attentions that can be triggered during the scan process.

TMP AUTO SETUP LIMIT—System pressure high limit—The automatic scan is aborted at 90% of the current system pressure high limit. The corresponding TMP-value is recommended. The system pressure high limit should be set as high as the filter can tolerate and is safe for the patient.

TMP AUTO SETUP LIMIT—Ratio $Q_{INF}/Q_B$=predetermined % value—In pre-dilution, the recommended infusion to blood flow ratio ($Q_{INF}/Q_B$) is 80-120%. The corresponding TMP-value minus 10% or 10 mmHg if TMP within −100 to +100 mmHg is recommended. Increasing the blood flow, adjusting the substitution volume or treatment time and/or selecting a more appropriate filter can obviate this limit situation.

TMP AUTO SETUP LIMIT—Ratio $Q_{UF}/Q_B$=predetermined % value—In post-dilution, the recommended maximum filtration to blood flow ratio ($Q_{UF}/Q_B$) is 30-40%. Increasing the blood flow, adjusting the substitution volume or treatment time and/or selecting a more appropriate filter can resolve this limit situation.

TMP AUTO SETUP—Dialysate flow changed—To obtain an optimal TMP, the dialysate flow has been automatically increased. This attention informs the operator of this fact and possible consequences such as increased concentrate consumption. Dialysate flow may be decreased to save concentrates, water, and energy.

TMP AUTO SETUP LIMIT—Dialysate flow limit reached—The main flow will automatically be increased during the scan process as needed. If no further adjustment is possible and the dialysate flow available for diffusion (in case of HDF treatment) is lower than the set blood flow in HDF-pre-dilution mode, the above attention will be triggered. The corresponding TMP-value is recommended.

TMP AUTO SETUP LIMIT—Substitution flow limit reached—If the maximum substitution flow rate is reached, this attention is triggered. The corresponding TMP-value will be recommended. The machine will temporarily enter volume controlled mode at maximum infusion rate until the infusion rate decreases.

TMP AUTO SETUP READY—Confirm new set TMP—The attention will be triggered at the end of the automatic scan to remind the operator to confirm the recommended TMP set point. If not confirmed within a predetermined time, the initial parameters (either set by the operator or found in initial volume control part of scan) will be recovered. In other embodiments no operator action is required and an auto-confirmation function is activated.

An algorithm to find optimum TMP is described. When TMP AUTO SETUP is started, the machine will temporarily enter volume controlled mode for 1 minute using the set parameters. Infusion rate will be very low to find a stable TMP to start the scan from (typically 50% of $Q_B$ if pre-dilution and 10% of $Q_B$ if post-dilution). Thereafter the resulting TMP will be used as initial value to the algorithm below:
1) pUFR=cUFR
2) Wait for a predetermined time period, e.g. 30 sec
3) Sample cUFR
4) If cUFR<pUFR then change direction of scan and reduce entity of step, for example step=−step/2
5) TMPset=TMPset+step
6) Repeat from 1) until step<predefined value, e.g. |2|*where*:

pUFR=previous UF rate (as saved in previous iteration)
cUFR=current UF rate (10 sec average)
step initial value is predefined, for example 50 mmHg
continuously supervise limits as identified above.

The above step 2) (waiting for a stable TMP) can be combined with or replaced by (and/or) a criteria to determine when a stable TMPset is reached from the measured TMP values in order to speed up the scan when taking small steps and allow more time for larger steps.

The invention claimed is:

1. A machine for extracorporeal blood treatment, comprising:
   a blood treatment device having a blood chamber and a fluid chamber, separated one from another by the semipermeable membrane,
   an extracorporeal blood circuit which comprises an arterial line, for taking blood removed from a patient to an inlet of the blood chamber, and a venous line, for returning treated blood from an outlet of the blood chamber to the patient,
   a device for ultrafiltration of a liquid through the semipermeable membrane of the blood treatment device,
   an infusion line connected to the extracorporeal blood circuit and provided with an infusion actuator for injecting into the extracorporeal blood an infusion flow of substitution liquid,
   a controller configured to perform the following operations:
      changing a transmembrane pressure across the semipermeable membrane of the blood treatment device;
      detecting a plurality of values of an infusion flow rate through said infusion line on changing said transmembrane pressure; and
      evaluating an optimal value of said infusion flow rate from a comparison of said plurality of values, the optimal value comprising at least one of equal to, and proximal to a maximum value of infusion flow rate through said infusion line as a function of said transmembrane pressure.

2. The machine of claim 1, wherein said controller is configured to receive a set value for a patient weight loss rate and to control the ultrafiltration flow rate of liquid through the semipermeable membrane and the infusion flow rate such that the ultrafiltration flow rate is equal to the sum of the patient weight loss flow rate and infusion flow rate.

3. The machine of claim 1, wherein said controller is configured to receive a set value for a patient weight loss rate and to calculate an optimal value for an ultrafiltration flow rate of liquid through the semipermeable membrane based on said evaluated optimal value of the infusion flow rate and on the set value for the patient weight loss rate.

4. The machine of claim 2, wherein said controller is configured to calculate an optimal value for an ultrafiltration flow rate of liquid through the semipermeable membrane based on said evaluated optimal value of the infusion flow rate and on the set value for the patient weight loss rate.

5. The machine of claim 3, wherein the controller is configured to perform the operation of selecting an optimal operating situation of said ultrafiltration device from said optimal value for the ultrafiltration flow rate.

6. The machine of claim 3, wherein said controller is configured to perform the operation of setting said ultrafiltration device on said optimal operating situation.

7. The machine of claim 1, wherein said optimal value of the infusion flow rate comprises the maximum value of infusion flow rate through said infusion line as a function of a transmembrane pressure.

8. The machine of claim 7, wherein said controller is configured to perform an operation of setting the transmembrane pressure as a function of the transmembrane pressure corresponding to said maximum of infusion flow rate.

9. The machine of claim 8, wherein the controller is configured to set the transmembrane pressure to a value corresponding to said maximum of infusion flow rate lowered by a predetermined percentage or by a predetermined amount if said transmembrane pressure is within a predetermined range.

10. The machine of claim 1, wherein before said operation of changing the transmembrane pressure across the semipermeable membrane, said controller is configured to perform the operation of imposing a volume control mode for a predetermined time period with an infusion rate of substitution liquid determined as a set value or as a function of the blood flow rate.

11. The machine of claim 1, wherein:
said ultrafiltration device comprises at least one fluid circulation pump which operates on a line of ultrafiltered liquid; and
said operation of changing the transmembrane pressure across the semipermeable membrane comprises a changing of the speed of rotation of the fluid circulation pump.

12. The machine of claim 1, comprising at least a sensor for measuring an ultrafiltration flow rate of liquid through said membrane, at least a sensor for measuring the infusion flow rate through the infusion line and at least a sensor for measuring the transmembrane pressure.

13. The machine of claim 1, wherein said operation of evaluating an optimal value of infusion flow rate comprises phases of:
determining at least one change in infusion flow rate caused by said change in transmembrane pressure across the semipermeable membrane;
checking whether said change in infusion flow rate and said change transmembrane pressure across the semipermeable membrane agree with a predetermined relation with a reference value;
generating a signal consequent to said checking phase.

14. The machine of claim 13, wherein said predetermined relation comprises a quotient between said change ultrafiltration flow rate and said change in transmembrane pressure across the semipermeable membrane.

15. The machine of claim 14, wherein said predetermined relation is satisfied if said quotient is less than a reference value.

16. The machine of claim 14, wherein said controller is configured to repeat said phases if said relation is not satisfied.

17. The machine of claim 1, wherein said controller is configured to periodically repeat said operations.

18. A machine for extracorporeal treatment of blood, comprising:
a blood treatment device having a blood chamber and a fluid chamber, separated one from another by the semipermeable membrane;
an extracorporeal blood circuit which comprises an arterial line, for taking blood removed from a patient to an inlet of the blood chamber, and a venous line, for returning treated blood from an outlet of the blood chamber to the patient;
an infusion line connected to the extracorporeal blood circuit and provided with an infusion pump for injecting into the extracorporeal blood an infusion flow of substitution liquid;
at least an ultrafiltration pump connected to said fluid chamber and configured for ultrafiltration of a liquid through the semipermeable membrane of the blood treatment device;
at least a blood pump for supplying a flow of liquid to the blood chamber of said blood treatment device;
at least a first sensor configured for measuring an ultrafiltration flow rate through said semipermeable membrane;
at least a second sensor configured for measuring an infusion flow rate through said infusion line;
at least a third sensor for measuring a transmembrane pressure across said semipermeable membrane;
a controller configured for performing the following operations:
determining at least one value of an infusion flow rate and at least one value of a transmembrane pressure in a first operating situation of said ultrafiltration pump;
commanding said ultrafiltration pump to change into a second operating situation which is different from the first operating situation thereof;
determining at least one value of an infusion flow rate and at least one value of a transmembrane pressure in said second operating situation;
checking whether said values related to two different operating situations satisfy a predetermined relation with a reference value;
generating a signal in consequence of said check;
depending upon the outcome of said check repeating or not the above-described operations; and
finding a maximum or nearly-maximum value for the infusion flow rate as a function of the transmembrane pressure.

19. The machine of claim 18, wherein said controller is configured to receive a set value for a patient weight loss rate and to control the ultrafiltration flow rate of liquid through the semipermeable membrane and the infusion flow rate such that the ultrafiltration flow rate is equal to the sum of the patient weight loss flow rate and infusion flow rate.

20. The machine of claim 18, wherein the controller is configured to set the ultrafiltration pump at an optimal operating situation corresponding to the maximum or nearly-maximum value for the infusion flow rate as a function of the transmembrane pressure.

21. The machine of claim 18, wherein said predetermined relation comprises a quotient between said change in infusion flow rate and said change in transmembrane pressure across the semipermeable membrane, and wherein said predetermined relation is satisfied if said quotient is less than a reference value.

* * * * *

UNITED STATES PATENT AND TRADEMARK OFFICE
CERTIFICATE OF CORRECTION

PATENT NO. : 8,771,215 B2
APPLICATION NO. : 13/331728
DATED : July 8, 2014
INVENTOR(S) : Claudio Tonelli et al.

Page 1 of 1

It is certified that error appears in the above-identified patent and that said Letters Patent is hereby corrected as shown below:

On the Title Page, in Item (73), please delete "Cambro Lundia AB" and insert therefor --Gambro Lundia AB--.

Signed and Sealed this
Twenty-fifth Day of November, 2014

Michelle K. Lee
*Deputy Director of the United States Patent and Trademark Office*